United States Patent
Pembroke et al.

(10) Patent No.: US 7,723,072 B2
(45) Date of Patent: May 25, 2010

(54) POLYPEPTIDE FACTOR FROM A THERMOPHILIC EUBACTERIAL SPECIES AND USE THEREOF IN THE PRODUCTION OF FUNCTIONAL, HETEROLOGOUS PROTEINS IN AN EXPRESSION HOST

(75) Inventors: Joseph Tony Pembroke, Castletroy (IE); Stefania Spada, Westbury (IE); John Gerard Wall, Westbury (IE)

(73) Assignee: University of Limerick, Limerick (IE)

( * ) Notice: Subject to any disclaimer, the term of this patent is extended or adjusted under 35 U.S.C. 154(b) by 31 days.

(21) Appl. No.: 11/944,511

(22) Filed: Nov. 23, 2007

(65) Prior Publication Data

US 2008/0227178 A1 Sep. 18, 2008

Related U.S. Application Data

(60) Division of application No. 11/322,333, filed on Jan. 3, 2006, now abandoned, which is a continuation of application No. 10/389,771, filed on Mar. 18, 2003, now abandoned.

(51) Int. Cl.
C12P 21/06 (2006.01)
C07H 17/00 (2006.01)
C07K 14/00 (2006.01)

(52) U.S. Cl. .................... 435/69.1; 536/23.1; 530/350
(58) Field of Classification Search .................. None
See application file for complete search history.

(56) References Cited

OTHER PUBLICATIONS

Knappik et al.; *Protein Engineering*, vol. 8, No. 1, pp. 81-89, 1995.
Wall et al.; *Protein Engineering*, vol. 12, No. 7, pp. 605-611, 1999.
McCafferty et al., *Nature*, vol. 348, pp. 552-554, 1990.
Spada et al., *Extremophiles*, vol. 6, pp. 301-308, 2002.
Spada et al.; *DNA Sequence*, vol. 11, No. 6, pp. 507-514, 2001.
Bothmann et al.; *Nature Biotechnology*, vol. 16, pp. 376-380, 1998.
Kuroda et al.; *Microbiol. Immunol.*, vol. 43, No. 2, pp. 115-125, 1999.
Nakai et al.; *Genomics*, vol. 14, pp. 897-911, 1992.
Krogh et al.; *J. Mol. Biol.*, vol. 305, pp. 567-580, 2001.
White et al.; *Science*, vol. 286: pp. 1571-1577, 1999.

*Primary Examiner*—Karen Cochrane Carlson
(74) *Attorney, Agent, or Firm*—Birch, Stewart, Kolasch & Birch, LLP

(57) ABSTRACT

A polypeptide factor derived from the thermophilic eubacterial species *Thermus thermophilus* has universal protein expression-assisting activity. The polypeptide factor has been named the CzrB protein active in full length or truncated form has the potential to act as a universal protein expression-assisting molecule which can increase the yields of all heterologous proteins produced in *E. coli* by a mechanism that is independent of the protein being expressed.

9 Claims, 8 Drawing Sheets

POLYPEPTIDE FACTOR FROM A THERMOPHILIC EUBACTERIAL SPECIES AND USE THEREOF IN THE PRODUCTION OF FUNCTIONAL, HETEROLOGOUS PROTEINS IN AN EXPRESSION HOST

The present application is a divisional application of application Ser. No. 11/322,333, filed on Jan. 3, 2006 (abandoned), which was a continuation application of application Ser. No. 10/389,771, filed on Mar. 18, 2003 (abandoned), priority of which is claimed under 35 U.S.C. §120 and the contents of which are hereby incorporated by reference.

FIELD OF THE INVENTION

This invention relates to the production of heterologous proteins in a host organism and to protein expression-assisting molecules which result in said heterologous proteins having functional activity, due to a correct folding thereof.

BACKGROUND AND PRIOR ART

The production of heterologous proteins in bacterial hosts such as the bacterium *Escherichia coli* (hereinafter referred to collectively as *E. coli* and exemplified by *E. coli* except where otherwise expressly stated) is a powerful tool in the generation of many important biotechnological and medical products. This technique involves inserting the DNA encoding the product in question into an *E. coli* cell and using the cell to convert the genetic information into a functional protein.

Research over the past 20 years has demonstrated the ability of *E. coli* to serve as the expression host for a wide variety of proteins from numerous sources, ranging from other Gram-negative bacteria to mammalian proteins.

Improvements to the basic technology include the development of secretion mechanisms, whereby polypeptides are exported to the periplasmic space or the extracellular medium, as required for their folding and/or activity. The periplasmic space is of particular interest to the biotechnologist in terms of heterologous protein production in *E. coli*, due to its oxidising environment. This allows the formation of disulfide bonds, which are essential for correct folding and activity of many mammalian proteins of medicinal and/or biotechnological interest, such as antibody molecules.

Other improvements to fundamental expression systems in *E. coli* include greater control of expression of heterologous proteins, and novel peptide tags encoded on expressed molecules to facilitate their detection and purification.

Due to its extensive genetic and biochemical characterisation, *E. coli* is frequently the organism of choice for heterologous protein production experiments. *E. coli* also exhibits simple fermentation pathways and has a short doubling time, which is also advantageous. Furthermore, the nutritional (and sterility) requirements of *E. coli* are uncomplicated, relative to higher organisms.

A major disadvantage of *E. coli* as an expression host, however, is the fact that the yields attainable with this organism are relatively low, while it frequently also exhibits difficulties in synthesising proteins derived from eucaryotic sources. These difficulties can take the shape of an inability to carry out particular post-translational modifications of the translated polypeptide or, more fundamentally, an inability of the *E. coli* cellular machinery to fold the peptide in the first place. In instances such as the latter, the available solutions have been to translate the polypeptide in *E. coli*, followed by refolding in vitro—a time-consuming and highly inefficient process—or to switch expression host to a higher organism which can carry out the expression efficiently, but with the concomitant loss of advantages of *E. coli*, as outlined above.

While *E. coli* carries out the process of gene expression and protein production very efficiently with its own, natural proteins, it is considerably less productive when expressing proteins from other species. This is most likely due to an inability to correctly fold the translated polypeptide, or to successfully transport it to the appropriate subcellular compartment for assembly or folding. Such a deficiency may result from the *E. coli* "synthetic machinery" being unable to recognise or act upon heterologous proteins due to differences in such proteins relative to *E. coli*'s native proteins. Alternatively, it may reflect an inability on the part of the host cells to express genes at the high levels demanded in such biotechnological experiments due to saturation of its normal gene expression and/or protein synthetic machinery. In such a scenario, the expressed protein typically forms large, insoluble aggregates consisting of multiple copies of the protein, which is non-functional and may be destroyed by the normal cellular machinery.

Furthermore, expression of heterologous genes in *E. coli* appears to frequently subject the cells to severe stress, leading to damage to the outer membrane of the host *E. coli* cell and leaking of the contents of the cell into the culture medium. This is typically followed by cell death via lysis of the *E. coli* cells.

This response of *E. coli* to expression of foreign genes has important implications for its potential in the production of a wide variety of heterologous proteins. With some foreign genes, *E. coli* has been found to be incapable of producing any functional protein; in cases in which *E. coli* folds the translated protein inefficiently or is overly stressed as a result of its expression, yields of the heterologous protein are dramatically reduced.

Researchers have attempted to overcome these problems with heterologous protein production in three main ways: i) genetic modification of the protein being expressed to improve its production in *E. coli*; ii) manipulation of the growth environment in order to reduce the stress on the expressing bacteria; and iii) co-expression in *E. coli* of natural folding-assisting molecules, termed chaperones, to improve production of the heterologous protein.

Genetic modification has proved successful with a number of proteins (Knappik, A. and Plückthun, A. (1995) *Prot. Eng.* 8:81-89; Wall, J. G. and Plückthun, A. (1999) *Prot. Eng.* 12:605-611) but remains severely limited by the fact that solutions to expression problems that result from mutagenic modification are likely to be highly specific for the particular protein being expressed—whereas solutions that could be applied to all heterologous proteins expressed in *E. coli* would eliminate the need for labour-intensive, highly time consuming mutagenic studies to be repeated for each protein being produced.

Manipulation of the growth environment, for example, by modifying nutrients and temperature, has been shown to have a mildly positive effect in a number of cases, but would ultimately be expected to improve expression of reasonably efficiently expressed proteins rather than being able to overcome serious difficulties of expression or folding of specific proteins. The approach that appears to offer most hope in terms of a generally applicable solution is that of co-expressing folding assisting molecules that will enable the host *E. coli* cells to correctly express any or all heterologous proteins, without the need for further optimisation. To date, no single molecule has been identified, however, that improves the production of all heterologous proteins studied and, thus, again the difficulty arises of having to individually optimise expression for each heterologous protein.

Thus, a generally applicable solution to expressing traditionally "difficult" proteins in *E. coli* would make a highly significant contribution to the field of heterologous protein production.

SUMMARY OF THE INVENTION

The invention provides a polypeptide factor derived from a thermophilic eubacterial species, said polypeptide factor having universal protein expression-assisting activity.

Preferably, the thermophilic eubacterial species is *Thermus thermophilus*.

Further, preferably, the polypeptide factor has an amino acid sequence defined as amino acid position 1 to amino acid position 291 in FIG. 2 (SEQ ID NO: 1). This polypeptide factor has been named the CzrB protein as hereinafter described. Said polypeptide factor described and characterised herein has the potential to overcome, by a mechanism that is independent of the protein being expressed, many of the difficulties associated with expressing proteins, more particularly eucaryotic proteins in *E. coli*.

According to one embodiment of the invention, the CzrB polypeptide factor is the full length protein of 291 amino acids having SEQ ID NO: 1 hereinbefore specified.

According to an alternative embodiment of the invention, the CzrB polypeptide factor is a truncated form of the CzrB protein, namely a polypeptide factor of 92 amino acids having SEQ ID NO: 2.

The CzrB protein from *T. thermophilus* either in its full length or truncated forms described herein has the potential to act as a universal protein expression-assisting molecule which can increase the yields of all heterologous proteins produced in *E. coli* as hereinafter described.

It is expected that the truncated version of CzrB, containing a putative 92 amino acids as opposed to the 291 of the mature CzrB protein will lead to significantly higher improvements in protein yields upon over-expression from a better regulated promoter. The truncated protein is less than one-third the size of the mature protein and thus is likely to accumulate to much higher levels and at lower metabolic expense to the expressing cell. Furthermore, the truncated protein is also unlikely to be inserted into the cell membrane in the host bacterial cell and, thus, less likely to interfere with normal cell functioning if expressed at greatly elevated levels in the cell under the control of a strong promoter.

The invention also provides an isolated DNA sequence encoding each of the polypeptide factors hereinbefore defined.

These isolated DNA sequences include a DNA sequence having SEQ ID NO: 3 encoding the polypeptide factor having SEQ ID NO: 1 and a DNA sequence SEQ ID NO: 4 encoding the polypeptide factor having SEQ ID NO: 2.

The invention also provides an isolated DNA sequence comprising the structural gene encoding the polypeptide factor having SEQ ID NO: 1 and a flanking sequence containing a control element for the expression of said polypeptide factor. The flanking sequence can be either a downstream sequence or an upstream sequence or both. One such sequence is SEQ ID NO: 5.

The invention also provides a method for increasing production of heterologous proteins in a bacterial host cell, which comprises contacting said bacterial host cell with an effective amount of the polypeptide factor as hereinbefore defined during the expression of said heterologous protein.

Preferably, the bacterial host cell is an *E. coli* host cell.

The invention also provides a vector comprising an isolated DNA sequence as hereinbefore defined.

The invention further provides a host cell containing an isolated DNA sequence as hereinbefore defined.

According to a further embodiment of the invention there is provided a method for increasing production of heterologous protein in a bacterial host cell, which method comprises cultivating said host cell under conditions permitting expression of a DNA sequence as hereinbefore defined.

Preferably, the heterologous protein is a eucaryotic protein.

According to a further embodiment of the invention there is provided a method for the production of heterologous functional protein in an *E. coli* host cell, said method comprising co-cultivating DNA for said heterologous functional protein with a DNA sequence as hereinbefore defined.

The invention also provides a method for the production of heterologous function protein in an *E. coli* host cell, which method comprises co-expression of a polypeptide factor as hereinbefore defined.

According to a further embodiment of the invention there is provided a method of reducing stress in an expressing bacterial cell, which method comprises co-expressing a heterologous protein and a polypeptide factor as hereinbefore defined.

According to a still further embodiment of the invention there is provided a method of optimising expression of a heterologous protein in an expressing bacterial cell, which method comprises co-expressing the heterologous protein and a polypeptide factor as hereinbefore defined.

The invention also provides an antibody to a polypeptide factor as herebefore defined.

The invention also provides a method of purifying a protein with universal protein expression-assisting activity, said method comprising contacting a cell extract with an antibody as hereinbefore defined.

The invention also provides a polypeptide factor as hereinbefore defined which has homology with metal ion efflux proteins from other eucaryotic species.

The invention also provides a polypeptide factor as hereinbefore defined which confers on *E. coli* increased resistance to heavy metal ions.

BRIEF DESCRIPTION OF FIGURES

FIGS. 2A and 2B is an alignment of the *T. thermophilus* CzrB amino acid sequence with homologues from a number of species as described in Example 2;

DETAILED DESCRIPTION OF PREFERRED EMBODIMENTS

Figure 1:
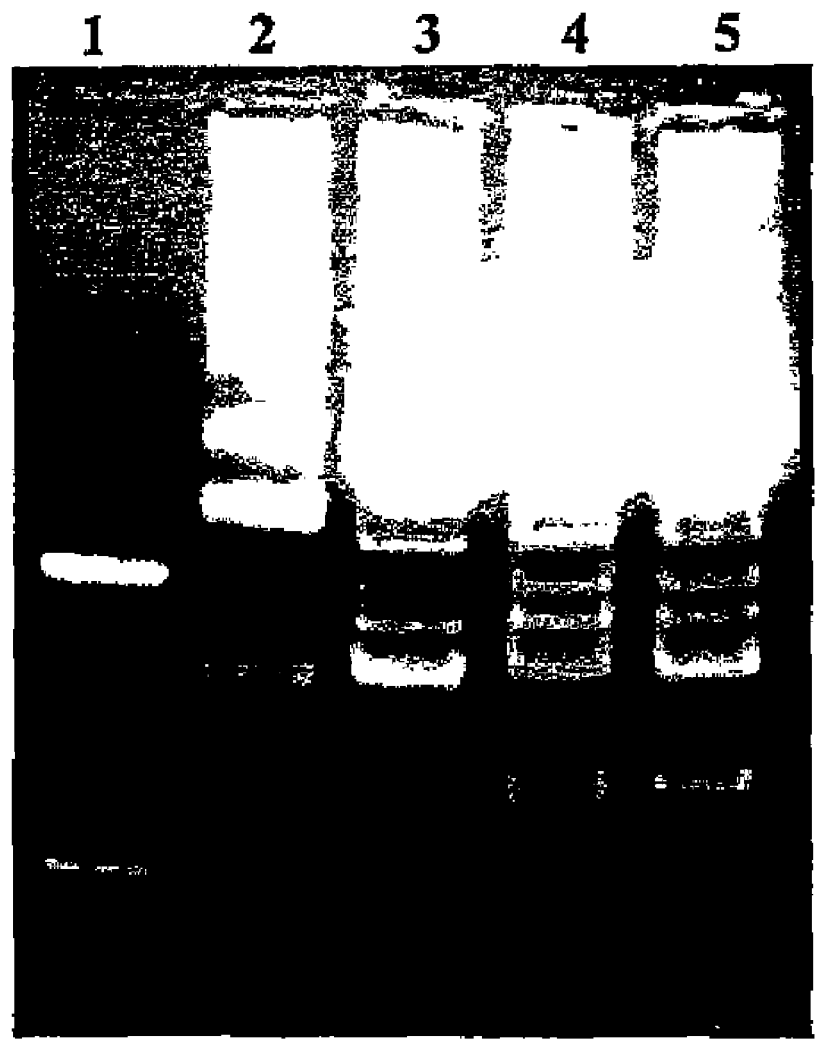
FIG. 1 is an agarose gel depicting the results of screening a bacteriophage library as described in Example 1.

Protein folding is highly sensitive to increases in temperature and thus a thermophilic bacterial species namely, the thermophilic eubacterium *T. thermophilus* was screened for possible novel or additional folding-assisting factors that might enable it to carry out folding effectively at high temperatures. Many proteins from *T. thermophilus* have also been functionally produced in *E. coli*, indicating recognition of its control elements by the mesophile. Furthermore, even though a thermophile, many of the enzymes of *T. thermophilus* function at *E. coli*'s growth temperature, allowing for phenotypic screening of gene libraries as hereinafter described.

The screening was based on identifying *T. thermophilus* molecules that might improve the ability of host *E. coli* cells to express a known, poorly folding antibody molecule. To this end phage display technology was carried out, in which antibodies were displayed on the surface of bacteriophage particles. A phage display system is an in vitro approach that mimics the human immune system by generating a large, diverse collection of antibody molecules, expressed on the surface of bacteriophage ("phage") particles, followed by selection of phage-antibody partners with desired binding specificities from the library. The displayed antibodies were first expressed in the host *E. coli* cells, leading to a requirement for correct folding for display. Bacteriophage particles were then subjected to affinity selection on an immobilised ligand, resulting in selection of antibody molecules that displayed an antibody of a particular binding specificity, depending on the identity of the immobilised ligand. While phage display technology is normally used to select antibodies from libraries of molecules of different binding specificities (McCafferty, J. et al (1990) *Nature* 348:552-554), as hereinafter exemplified in the same antibody was cloned onto all phage particles in accordance with the present invention. A genomic DNA library, generated from *T. thermophilus*, was also cloned into the expressing *E. coli* cells. Thus, the difference between *E. coli* clones in the resultant library was merely the identity of the *T. thermophilus* DNA contained within the cells, such that affinity selection of one bacteriophage particle over another would be determined by the *Thermus* gene and, in turn, its effect on the expression of the displayed antibody in the host *E. coli* cells.

Replication in *E. coli* gives rise to random mutations in the isolated antibodies with the result that affinity maturation (selection of higher affinity molecules) occurred upon repeated cycles of antigen binding and re-infection. Critically, the production of phage particles in the host *E. coli* cells in this manner necessitates correct folding of not only the native phage proteins but also the displayed recombinant protein if it is to be effectively displayed and, thus, affinity selected.

Thus, a modified phage display system, in which all phage particles expressed the same, poorly-folding antibody molecule on their surface was utilised in accordance with the present invention. A chromosomal DNA library from *T. thermophilus* was also cloned into the phage vector containing the antibody fragment. As all phage particles contained the same antibody fragment—and should therefore display antibodies with identical affinities for the immobilised ligand—selection should be dependent on the efficiency of folding (and, thus, efficiency of display) of the molecule rather than the strength of the binding event. Thus, any *T. thermophilus* gene encoding a protein that facilitated expression of the recombinant antibody fragment would lead to improved production and display of the cloned antibody fragment and lead in turn to isolation of that clone from the phage antibody library (Spada, S. et al (2002) *Extremophiles* 6:301-8).

Screening of the *T. thermophilus* library led to the isolation of the czrB gene, both in a full-length and a truncated form. Sequence analysis indicated homology with metal ion efflux proteins from a number of species. The gene was re-cloned to eliminate flanking partial gene sequences in the isolated clones and the resultant clones were analysed in a number of ways. *E. coli* clones containing the czrB gene were found to exhibit increased resistance to cadmium and zinc, with zinc, cadmium and cobalt all found to induce the resistance to zinc ions. Measurement of intracellular zinc concentrations over time indicated that the CzrB protein was active in efflux of zinc from the *E. coli* cells as a mechanism of mediating this resistance. Furthermore, clones containing the czrB gene were shown to grow more rapidly and exhibited delayed cell lysis than clones lacking the gene, when this growth was associated with antibody and bacteriophage production. This led in turn to higher antibody yields in the former cells. Further analysis of this effect indicated that the CzrB protein did not appear to interact at the molecular level with either the antibody or the bacteriophage particles and could thus be considered a true, general "stress reliever" of the *E. coli* cells. For this reason it is envisaged that the polypeptide factors according to the invention will have widespread application in increasing production levels of heterologous proteins produced in *E. coli* in general, as stated above.

The *T. thermophilus* gene and gene product described herein have the potential to be developed into a universal cure for difficulties associated with the expression of eucaryotic proteins in *E. coli*. While other workers have identified molecules and techniques that assist the production of individual proteins in *E. coli* expression hosts, a critical aspect of the present invention is the observation that the effects on the expressing host—of improving growth, delaying cell lysis and, thus, increasing yields of heterologous protein produced—are independent of the identity of the protein being produced. Thus, coexpression of a DNA sequence according to the invention in currently available periplasmic expression vector systems is expected to confer such growth improvements on *E. coli* cells expressing any heterologous protein, irrespective of its source, with concomitant improvements in protein yields.

While the czrB gene was expressed under the control of its own, natural promoter as described in the following Examples, it will be clear to those skilled in the art that further improvements in *E. coli* cell growth and protein yields can be expected if czrB is expressed from a stronger, more standard promoter used in cloning and expression experiments, such as for example Plac. This would be expected to yield significantly higher CzrB levels in the expressing cell, which would be likely to exhibit increased benefits in terms of heterologous protein expression and yields.

The invention will be further illustrated by the following Example

Example 1

Construction and Screening of the *T. thermophilus* Genomic Library

The *T. thermophilus* genomic library was constructed as follows (Spada S. et al (2001) *DNA Seq* 11:507-514): a 5 ml culture of *T. thermophilus* KT8 was harvested at an $OD_{600}$ of 1.8 and the cell pellet was resuspended in 0.5 ml STE buffer (10 mM Tris, 100 mM NaCl, 1 mM EDTA, pH 8.0). RNase A was added to a final concentration of 100 µg/ml, SDS to 8.5 mg/ml and proteinase K to 100 µg/ml. Incubation for 2 h at 37° C. was followed by two phenol extractions, three phenol/chloroform/isoamyl alcohol extractions, ethanol precipitation and resuspension in 100 µl TE buffer. The *T. thermophi-*

*lus* chromosomal DNA was partially digested using Sau3AI restriction enzyme in order to maximise the yield of DNA fragments in the 1-5 kb range. Fragments in this size range were purified using a QIAEXII agarose gel DNA extraction kit (Qiagen) and cloned into a BglII-digested pHB102 phagemid vector containing the poorly-folding anti-fluorescein-isothiocyanate (FITC) scFv antibody fragment (Bothmann, H. and Plückthun, A. (1998) *Nat Biotechnol* 16:376-380). The library was transformed into *E. coli* XL1-Blue cells and the resultant library was estimated by NotI digestion to contain in the region of $1.1 \times 10^4$ clones. As this was calculated to be in excess of the size required to contain all *T. thermophilus* genes, based on the size of the *T. thermophilus* genome, screening of the library was initiated.

Phage production was induced overnight in *E. coli* cells harbouring the *Thermus* library and five rounds of fluorescein-isothiocyanate (FITC), the antigen recognised by the displayed antibody fragment, were carried out as follows. *E. coli* cells harbouring the *Thermus* library were inoculated to an $OD_{600}$<0.05 in 10 ml 2xYT medium containing tetracycline (15 μg/ml), additional salts (8.6 mM NaCl; 2.5 mM KCl; 10 mM $MgCl_2$) and 0.4% glucose. After 1 h at 37° C., 30 μg/ml chloramphenicol was added, followed by $10^{10}$ pfu of helper phage (VCSM13 helper phage; Stratagene) at an $OD_{600}$ of 0.5. Incubation at 50° C. for 5 min was followed by the addition of 50 ml 2xYT containing tetracycline, chloramphenicol, additional salts and 0.5 mM isopropyl-β-D-thiogalactoside (IPTG). The culture was shaken at 40° C. for 2 h and, after the addition of 30 μg/ml kanamycin, grown for a further 12-14 h at 40° C. Phage particles were precipitated from culture supernatants by two PEG precipitation steps and resuspended in 1 ml PBS (8 g NaCl, 0.24 g $KH_2PO_4$, 1.44 g $Na_2HPO_4$, 0.2 g KCl in 1 L, pH 7.4). Immunotubes (Nunc) were coated overnight at 4° C. with 1 μg/ml fluorescein-isothiocyanate coupled to bovine serum albumin (FITC-BSA) (Bothmann, H. and Plückthun, A (1998) supra) in PBS. Blocking was with 5% skimmed milk in PBST (PBS containing 0.05% Tween-20) for 2 h at 37° C., followed by dilution of 800 μl of the phage solution in 3.3 ml of 2% skimmed milk in PBST and incubation in the tubes for 2 h at 25° C. Twenty washes with PBST and two with PBS were followed by elution of bound particles for 10 min at room temperature using 1 ml 0.1 M glycine/HCl (pH 2.2). The eluate was neutralised immediately with 60 μl of 2 M Tris and used for reinfection of *E. coli*; this procedure was repeated for five rounds of phage selection on immobilised FITC and reinfection ("panning"). After each panning round DNA from the phage pool was digested with NotI to check for enrichment of *Thermus* DNA inserts. After the third round, a DNA fragment of approximately 1.2 kb began to appear in the digested library pool, as well as a less intense band of 1.8 kb which became considerably enriched by the fifth panning round as shown in FIG. 1.

In FIG. 1 the molecular weight marker (DNA Molecular Weight Marker XIV from Roche Applied Science) is in lane 1 and control, undigested phagemid DNA in lane 2. The result of restriction analysis of phage pools from panning rounds 3, 4 and 5 are shown above in lanes 3-5, respectively.

These results were a clear indication that selection of specific clones was occurring in the library. Therefore, after the fifth panning round, 30 individual clones were isolated and analysed by NotI digestion in order to determine the size of their cloned *T. thermophilus* gene. One clone had an insert of approximately 1.8 kb, 2 clones had inserts of 1.2 kb (which corresponded to the sizes observed in the library pool analysis), 25 clones had inserts of between 50 and 280 bp and the remaining 2 clones no insert. As approximately 90% of clones had been determined to contain inserts of 1-5 kb in analysis of the original library, the smaller inserts observed in 27 of 30 clones after panning was interpreted as evidence for a strong selective pressure against *E. coli* cells retaining large sections of DNA which provided no benefit to the cell. It was speculated, therefore, that the *T. thermophilus* genes retained (and selected) by *E. coli* clones under such conditions should confer a strong advantage upon the cells and the basis of that selective advantage was then determined in the 3 clones identified with the larger *T. thermophilus* DNA inserts.

Example 2

Identification and Analysis of *T. thermophilus* czrB

Clones containing the larger fragments described in Example 1 were sequenced to identify the isolated *Thermus* genes. Sequencing of the isolated 1.8 kb clone revealed an insert of 1743 bp, containing a single complete open reading frame (ORF) of 876 bp. BLASTx analysis of the complete ORF using the EMBL database revealed homology to cation efflux system proteins, mostly termed Czr (for cadmium-zinc resistance) or CzcD (for cadmium-zinc-cobalt resistance), from a variety of organisms. Based on experimental analysis, the *T. thermophilus* gene was named czrB, after the *Staphylococcus aureus* gene (Kuroda, M. et al (1999) *Microbiol Immunol* 43:115-125). Multiple sequence alignments were generated with homologous proteins using CLUSTALw as depicted in FIG. 2.

Figure 2A:
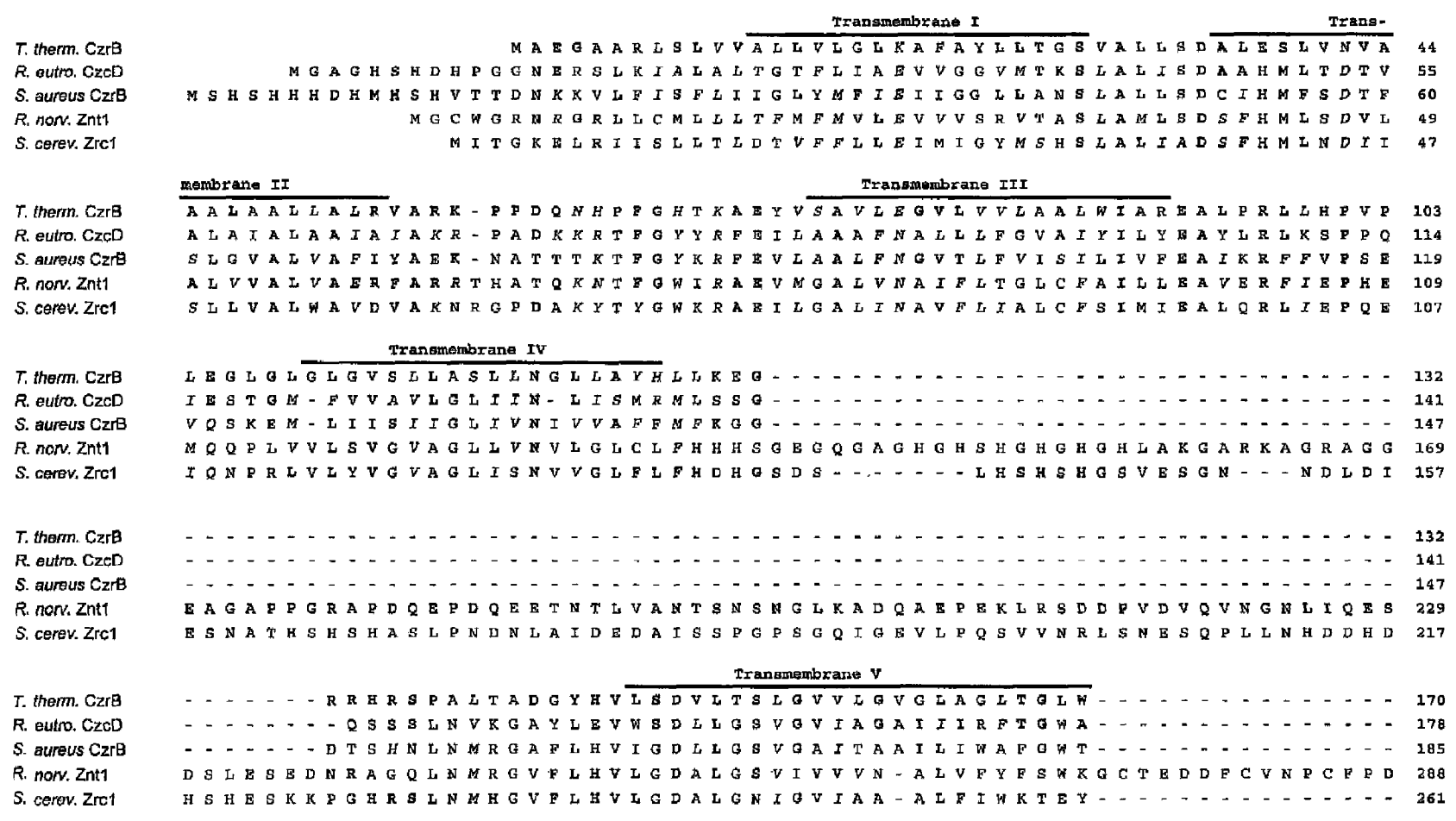
Figure 2B:
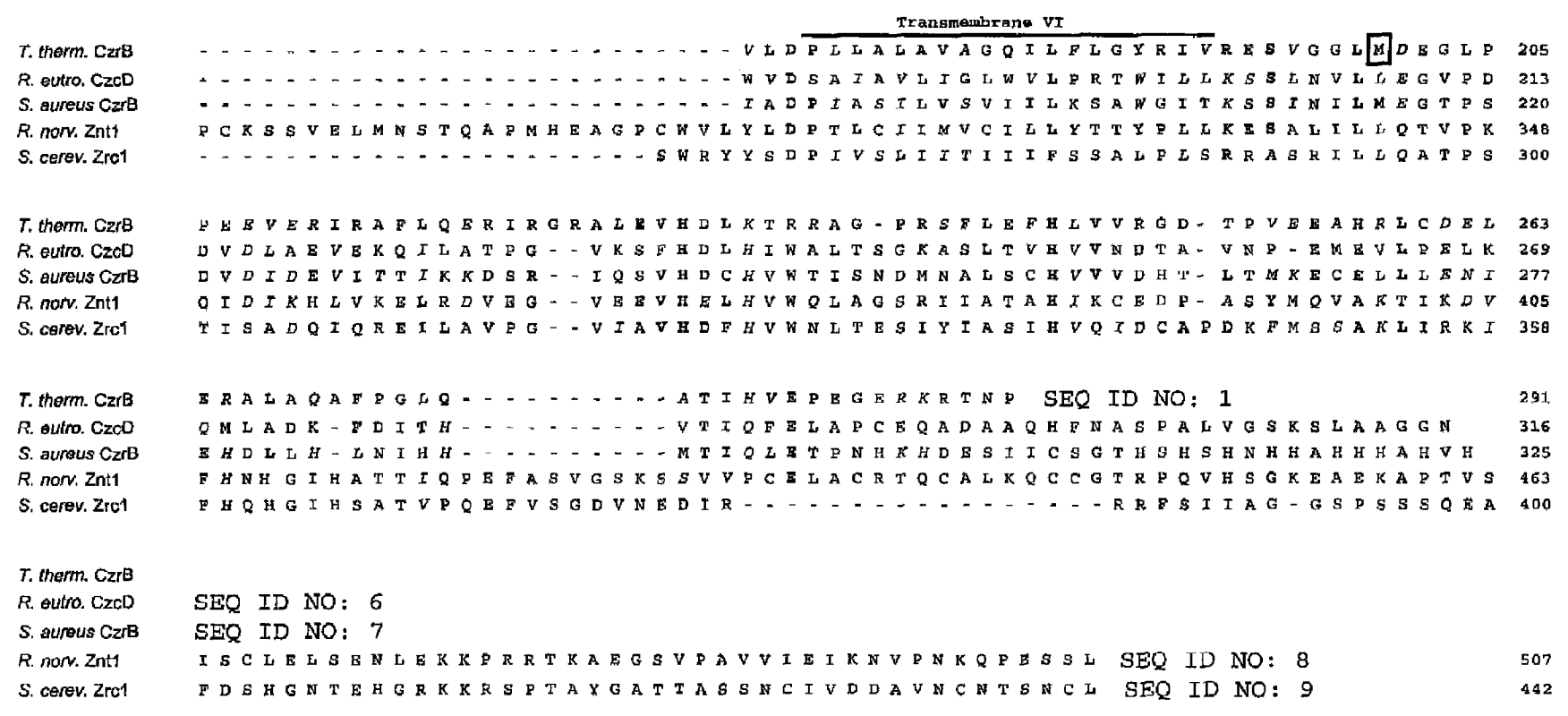

FIG. 2 shows the alignment of the *T. thermophilus* CzrB amino acid sequence identified herein with homologues from *Ralstonia eutropha* (CzcD, accession number P13512), *S. aureus* (CzrB, Q9ZNF5), rat (*Rattus norvegicus*) (Znt1, Q62720) and *Saccaromyces* cerevisiae (Zrc1, P20107). Emboldening indicates residues identical to the *T. thermophilus* sequence and italics residues homologous to the *Thermus* sequence. The putative translation start site for the partial czrB gene isolated from the library ($Met_{200}$) is boxed.

Of the known homologues, only those from rat, *S. cerevisiae*, *R. eutropha*-like CH34 (previously *Alcaligenes eutrophus* CH34) and *S. aureus* have been phenotypically characterised, with the main structural difference between the proteins being the extended loops between putative transmembrane segments in eucaryotic species. PSORT II (Nakai, K. and Kanehisa, M. (1992) *Genomics* 14:897-911) was employed for subcellular localisation predictional analysis, which envisaged the *Thermus* protein as a cytoplasmic membrane protein of molecular mass 31233 Da, while a modified hidden Markov model was utilised for prediction of transmembrane helices (Krogh, A. et al (2001) *Mol Biol* 305:567-580) and indicated that it contained six putative membrane-spanning α-helices, of which the 4 N-terminal spanners were highly hydrophobic, features conserved in other CzcD-like proteins. The *Thermus* structural gene also had a % GC content and amino acid composition typical of genes from thermophilic species.

As the sequence of the *T. thermophilus* gene had not previously been reported, it was re-amplified from the *T. thermophilus* genomic DNA, cloned into pUC19 and re-sequenced in order to confirm the original sequence. As well as confirming the original sequence, this re-cloning served to eliminate partial structural genes on either side of the czrB gene in the original clone, in order to eliminate possible interfering materials in subsequent characterisation of the effects of CzrB. 100 bp was retained upstream and 78 bp downstream of the czrB gene in this re-cloning, however, as these regions were expected to contain any control elements from the *T. thermophilus* chromosome, thus allowing study of not only the CzrB protein, but also the control of its expression in vivo.

Sequencing of the two 1.2 kb clones isolated during library screening revealed identical partial copies of czrB, encoding the 108 C-terminal amino acids of the 291 residue protein. It was determined that the first consensus ATG in this truncated czrB gene occurred at $Met_{200}$ and was closely preceded by a putative ribosome binding site; therefore, it was concluded that translation most likely begins in these truncated genes at residue 200 and yields a 92 amino acid peptide that corresponds to the C-terminal, cytoplasmic tail of the mature CzrB molecule shown in FIG. 2. Subcellular localisation analysis of this putative polypeptide (Nakai, K. and Kanehisa, M. (1992) supra) predicted it to form a soluble, cytoplasmic molecule in the cell.

Example 3

Heavy Metal Analysis

Given that the czrB gene and its truncated form that were isolated from the phage display screening described in Example 2 showed homology to cation efflux proteins, we investigated whether the isolated clones exhibited activities similar to those reported for homologous proteins in other species. Minimal inhibitory concentrations (MICs) for metal cations were therefore measured for cells with and without the cloned czrB gene in order to investigate whether the *T. thermophilus* protein protected host *E. coli* cells grown in high concentrations of heavy metals. *E. coli* clones were grown in LB medium containing 100 µg/ml ampicillin and 25 µg/ml streptomycin for 90 min at 37° C. This was carried out with and without addition of 165 µM $ZnCl_2$, 220 µM $CoCl_2$ or 80 µM $CdCl_2$ (chosen as approximately 10% of MICs). Following dilution in LB, $10^3$-$10^4$ cells were spread on LB agar (plus ampicillin and streptomycin) containing $ZnCl_2$ (at concentrations ranging from 1.4 mM to 2.9 mM at 0.1 mM intervals), $CoCl_2$ (1.7 mM to 2.2 mM with 0.1 mM steps) or $CdCl_2$ (from 0.6 mM to 1.2 mM with 0.1 mM steps). Growth of *E. coli* was measured after 24 h and 40 h, with MICs of the three metals defined as the lowest concentrations not allowing detectable *E. coli* growth after 40 h at 37° C. MIC determinations were carried out three times with each clone and metal ion. *E. coli* cells containing the *T. thermophilus* czrB gene exhibited a significantly higher MIC for $Zn^{2+}$ than cells containing pUC alone, while the cadmium MIC increased only slightly and cobalt resistance was unaffected by the presence of czrB as shown in Table 1.

TABLE 1

Minimal inhibitory concentrations (MICs) of $ZnCl_2$, $CoCl_2$ and $CdCl_2$ determined for *E. coli* JM83, JM83 containing pUC and JM83 containing pUC with cloned czrB.

| Clone | pre-induction | MIC (mM) | | |
|---|---|---|---|---|
| | | Zinc | Cobalt | Cadmium |
| JM83 | none | 2.0 | 2.1 | 0.9 |
| +pUC | none | 1.6 | 2.1 | 0.9 |
| +pUC | zinc | 1.6 | 2.1 | 0.9 |
| +pUC | cobalt | 1.6 | 2.1 | 0.9 |
| +pUC | cadmium | 1.6 | 2.1 | 0.7 |
| +pUC-czrB | none | 1.9 | 2.1 | 1.0 |
| +pUC-czrB | zinc | 2.5 | 2.1 | 1.0 |
| +pUC-czrB | cobalt | 2.1 | 2.1 | 1.1 |
| +pUC-czrB | cadmium | 2.2 | 2.1 | 0.9 |

Induction of metal resistance in *E. coli* cells carrying czrB was found to have a significant effect on metal tolerance of cells over the subsequent growth period, but with no difference observed between relative MICs measured after 24 or 40 h. Resistance to zinc mediated by the *Thermus* czrB could be induced by pre-incubation of *E. coli* cells with zinc, cadmium or cobalt as shown in Table 1. Thus, curiously, the *Thermus* protein appears to recognise cobalt and yet not to transport the cation. The ability to induce zinc tolerance was considerable, with the zinc MIC increasing from 1.6 mM (no czrB) to 1.9 mM (with czrB) to 2.5 mM (with czrB pre-induced by zinc) in the *E. coli* cells. The ability to induce cadmium resistance was poor, however, with only slight, non-statistically significant, increases in MIC inducible with cadmium or cobalt, and no detectable effect with zinc. No increase in zinc MICs was seen upon pre-incubation of wild-type *E. coli* cells with zinc.

Figure 3:
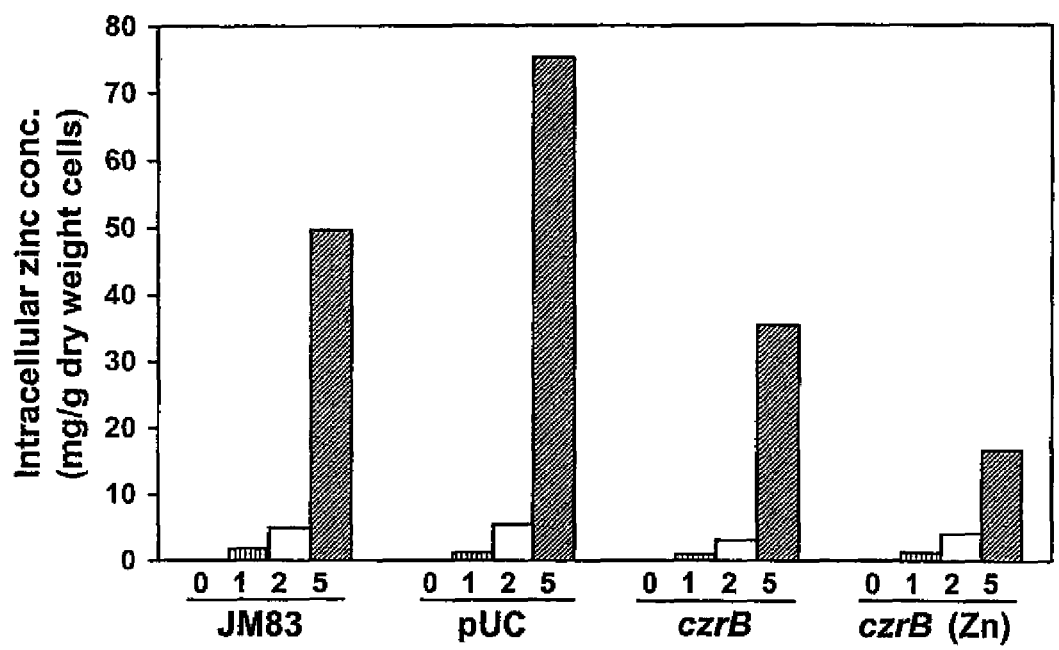
FIG. 3 is a graph of intracellular zinc concentration (mg/g dry weight cells) for a number of *E. coli* clones as described in Example 3.

Metal resistances of the type observed with the czrB clones can be the result of metal sequestering or modification of metal transport processes. However, based on reports of CzrB homologues in other organisms it was postulated that the protein CzrB provided resistance to heavy metal ions by an efflux mechanism rather than by metal sequestering. Therefore, the ability of the *T. thermophilus* CzrB protein to pump zinc ions out of the *E. coli* cells in which it was expressed was investigated. Intracellular zinc concentrations were measured as follows: *E. coli* clones were grown at 37° C. in LB medium (100 µg/ml ampicillin, 25 µg/ml streptomycin) in the presence or absence of 165 µM $ZnCl_2$ until an $OD_{600}$ of 1.0 was reached. After addition of 1, 2 or 5 mM $ZnCl_2$, growth was continued for 30 min, 1 h or 2 h, with control cultures grown in the absence of $ZnCl_2$. Samples (20 ml) of each culture were centrifuged at 8000 g for 20 min at 4° C. and cell pellets were washed in 4 ml LB medium and in 4 ml 0.1 N $HNO_3$. Following 15 min at 121° C., pellets were dissolved in 500 µl of $H_2SO_4$ and approximately 150 µl of $HNO_3$ was added dropwise until the solution went clear. Six ml of water was added, followed by centrifugation at 8000 g for 25 min. The zinc concentration was measured in the supernatant using an atomic absorption spectrophotometer (Varian SpectrAA-400 Plus), with standard solutions prepared immediately before use from commercial standards (Fisher Scientific). A calibration curve relating $OD_{600}$ to cell dry weight was used to calculate intracellular zinc concentrations at time of harvesting. The results are shown in FIG. 3 which depicts a quantification of intracellular zinc levels in *E. coli* clones: JM83 ("JM83"), JM83 containing pUC ("pUC"), and JM83 containing pUC-czrB without ("czrB") and with ("czrB (Zn)") a zinc pre-induction step. Results of 1 h incubations in 0, 1, 2 and 5 mM extracellular zinc concentrations are shown.

As indicated in FIG. 3, the presence of czrB was found to significantly reduce the levels of zinc in *E. coli* cells, whereas pUC alone led to elevated intracellular zinc levels. These results indicated that increased metal resistance was mediated by modification of either influx or efflux activity. This effect was particularly evident at high extracellular zinc concentrations that led to elevated initial intracellular concentrations in *E. coli* cells. Pre-exposure of cells to zinc further reduced cellular levels in czrB clones in high zinc environments, indicating an inducible resistance mechanism, as observed in MIC experiments.

Figure 4:
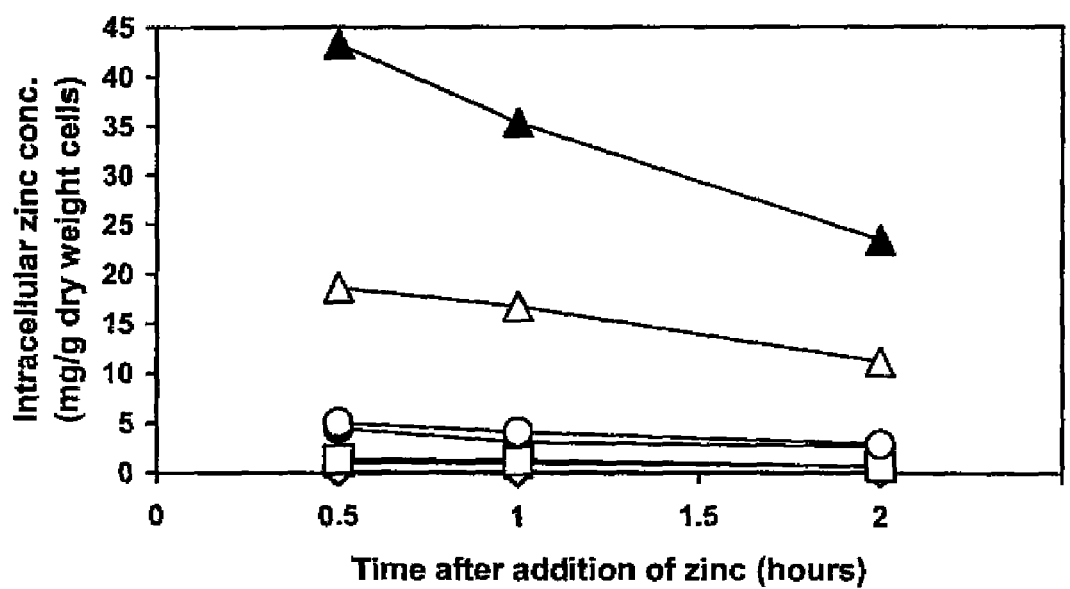
FIG. 4 is a graph of intracellular zinc concentration (mg/g dry weight cells) versus time (h)) following zinc efflux from *E. coli* cells containing *T. thermophilus* czrB as described in Example 3.

A time course experiment was carried out to distinguish between reduced influx and increased efflux as the cause of the reduced cellular accumulation of zinc. The results are shown in FIG. 4 which depicts the results of an analysis of zinc efflux from *E. coli* cells containing *T. thermophilus* czrB. Clones shown were grown in 0 mM (triangles), 1 mM (circles), 2 mM (squares) or 5 mM (diamonds) $ZnCl_2$. Empty symbols show the same clones subjected to pre-exposure to 165 µM ZnCl$_2$ prior to analysis. Intracellular zinc concentrations decreased significantly over the analysis period, with the rate of ion removal increased upon pre-exposure of cells to zinc, indicating that the protective mechanism of czrB involves an inducible process of efflux of metals from the cell.

Example 4

Investigation of Effects on Heterologous Protein Production

The strong selection of clones that had eliminated all or part of their *Thermus* insert during phage panning (27 of 30 clones analysed were found to have inserts of <300 bp) indicated that czrB exerted a strong positive effect on its host cells merely to be retained throughout library screening. In addition, the czrB gene was contained in all 3 large-insert clones selected from the library, in one case as a full-length molecule and in the other two as identical partial sequences. The observed effects of czrB on metal resistance of host *E. coli* cells were of no apparent advantage (or relevance) during the phage display procedure. An investigation of why czrB, in both its full-length and partial forms, should be so strongly selected in the library screening experiments was then investigated. Thus, *E. coli* clones were analysed under recombinant antibody and phage production conditions in order to investigate the basis of the effect of CzrB. These experiments were designed to determine if (i) czrB led to increased phage titres in host *E. coli* cells; (ii) czrB led to improved folding of the recombinant anti-FITC antibody, co-expressed in the host *E. coli* cell; and (iii) czrB had any effect on the growth of *E. coli* cells expressing the anti-FITC antibody.

Figure 5:
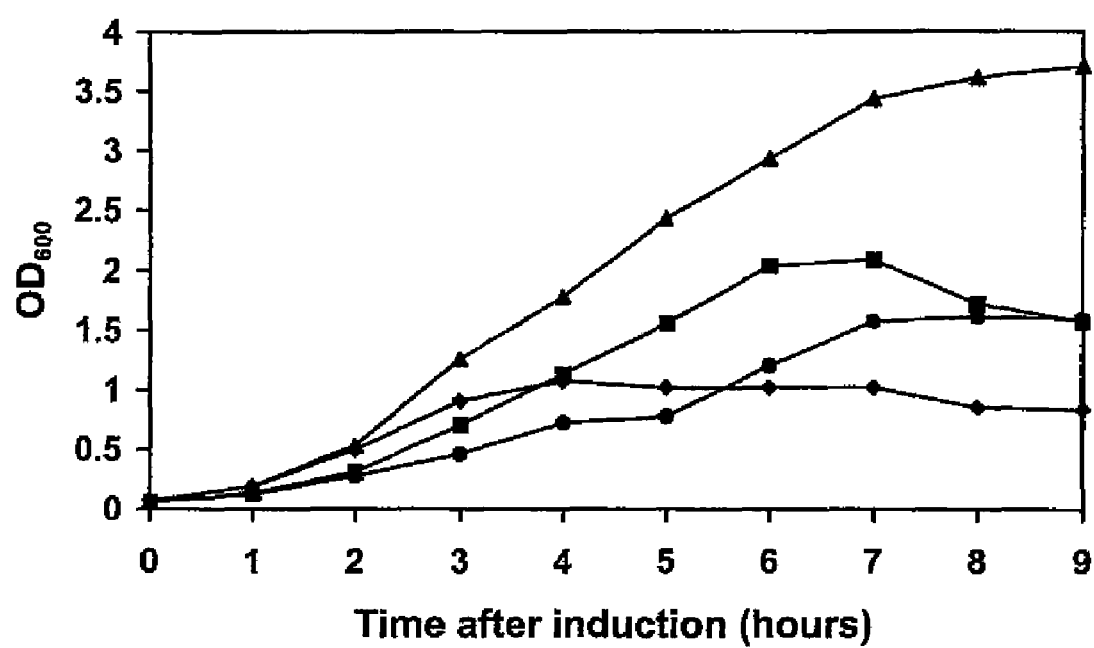
FIG. 5 is a graph of O.D. 600 versus time after induction (hours) depicting growth of *E. coli* clones containing *T. thermophilus* czrB as described in Example 4.

*E. coli* cells infected with phage were grown as described in Example 1. The OD$_{600}$ was read at hourly intervals for the first 8-10 h after induction. The results are shown in FIG. 5 which depicts growth of *E. coli* clones containing *T. thermophilus* czrB. Growth characteristics of *E. coli* clones containing pHB102 phagemid vector alone (circles) or with czrB (triangles), a partial czrB gene (squares) or random *T. thermophilus* DNA (diamonds) as an insert are shown. The experiment was carried out during bacteriophage and recombinant antibody production in the *E. coli* cells. This experiment revealed that czrB-containing clones grew considerably better than cells containing just the phagemid vector with delayed cell lysis and greater than 2-fold higher cell densities attained. These cell density differences were maintained after 22 h of induction (data not shown) and this improved growth of czrB-containing clones is believed to account for selection of the gene from the library. Isolated clones containing the partial czrB insert exhibited growth characteristics intermediate between the full-length czrB clone and cells containing the phagemid vector, while a randomly selected control clone with a 2 kb insert displayed significantly poorer growth than clones containing the vector alone. This result also provided an insight into how the original library became biased in favour of clones containing small sized or no *Thermus* inserts in the absence of a phenotypic benefit associated with the cloned DNA.

Example 5

Determination of Phage Titers and the Amount of Antibody Displayed in Funcational Form on the Phage Surface Culture samples from the growth experiment described in Example 4 were also collected to determine both phage titers and the amount of antibody displayed in functional form on the phage surface. Individual clones were analysed by restriction digestion after 22 h of induction to confirm that they contained both the *Thermus* insert and the recombinant antibody gene. Clones were analysed in at least three independent experiments and while absolute OD values, phage titers and ELISA readings varied between experiments, the respective patterns of growth and production exhibited by individual clones remained highly consistent throughout ELISA analysis was used to determine the effects of co-expressing the czrB gene on the functionality of the phage-displayed antibody protein. Immunoplate wells (Nunc) were coated with 100 µl of FITC-BSA and blocked with 5% skimmed milk in PBST. After washing, 100 µl of phage solutions containing 0.5% skimmed milk were added and incubated for 2 h at 25° C. Phage particles were detected using a peroxidase-conjugated anti-M13 antibody (1:3000 in PBST; Amersham Pharmacia Biotech Inc.) and development was carried out using a BM Blue POD soluble substrate (Roche Diagnostics). After stopping the reaction using 25 µl of 1 N H$_2$SO$_4$, the absorbance was read at 405 nm. *E. coli* cultures containing czrB were found to exhibit two-fold higher phage titres and to produce more than twice the amount of functional antibody as cultures containing the vector alone. The results are depicted in FIGS. 6 and 7.

Figure 6:
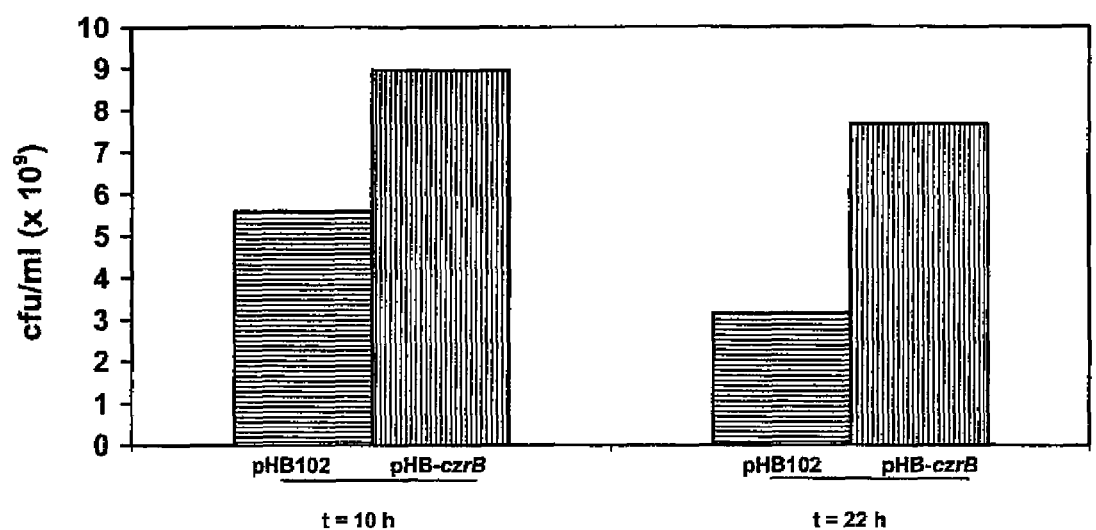
FIG. 6 depicts phage titers (cfu) of clones containing pHB102 phagemid vector or pHB102-czrB determined 10 and 22 h. after induction as described in Example 5.

FIG. 6 depicts phage titers of clones expressing czrB. The phage titers of clones containing pHB102 phagemid vector or pHB102-czrB expressed as colony forming units (cfu) were determined 10 and 22 h after induction.

Figure 7:
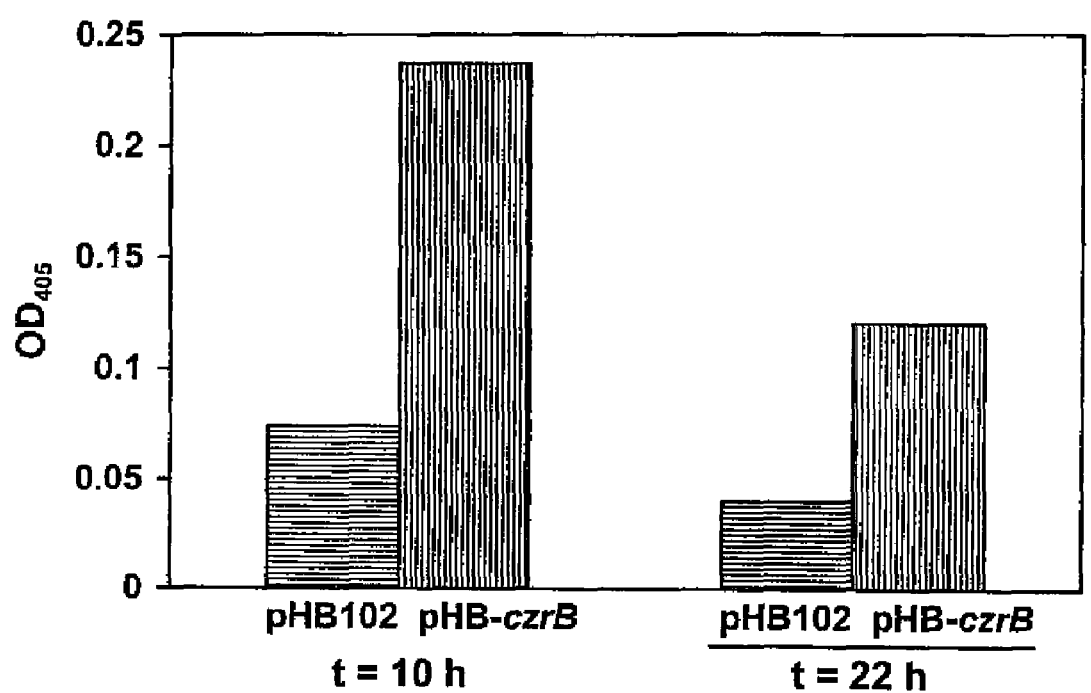
FIG. 7 depicts O.D. 405 resulting from anti-FITC ELISAs carried out on the clones of FIG. 6 determined 10 and 22 hr. after induction as described in Example 5.

FIG. 7 depicts ELISA analysis of clones expressing czrB. Anti-FITC ELISAs were carried out on the same clones as in the case of FIG. 6 so as to investigate the functionality of bacteriophage-displayed FITC-binding antibody fragments. Results are shown for samples taken 10 and 22 h after induction.

Cells containing the partial czrB gene showed signals intermediate between the full-length gene and the control culture in both phage titre and ELISA studies (data not shown). This led to the conclusion that, while the transmembrane domains of the *T. thermophilus* protein are required for its full effect to be achieved, the putative cytoplasmic tail of CzrB alone makes a significant contribution to the beneficial effects of the protein observed in *E. coli*. While the truncated CzrB construct according to the invention was not tested in efflux experiments, other workers have found that the C-terminal 62 and 72 amino acids from rat ZnT-1 and *R. eutropha* CzcD, respectively, are inessential for the protein's role in cation efflux, suggesting that the roles of *T. thermophilus* CzrB in metal efflux and in facilitating *E. coli* growth under recombinant protein production conditions occur via distinct mechanisms. Finally, the increased yields observed with both the full length and truncated versions of czrB were proportional to, and therefore apparently directly attributable to, the increased cell densities observed in *E. coli* cultures containing czrB, indicating that the czrB gene product appeared to have no direct effect on cellular antibody expression or bacteriophage production. Rather, its effect appeared to reside in relieving the physiological stresses typically associated with recombinant protein production in *E. coli*, thus allowing improved growth, higher culture densities and increased yields of recombinant protein in the cultures.

To investigate this theory further, czrB was expressed from a lac promoter in a standard pUC-based expression vector, in the absence of bacteriophage particles and the recombinant antibody used in experiments thus far. The same pattern of *E. coli* cell growth, relative to cells containing the vector alone, was observed upon P$_{lac}$ induction (data not shown), confirming that the effect of CzrB appears to be to improve E. coli physiology, at least in the presence of pUC-based vectors, rather than to interact directly with the antibody or bacteriophage molecules in the cell. This raises the possibility that CzrB, in its full length form or as a truncated version, might function as an "universal chaperone", which would facilitate the expression of any recombinant or heterologous proteins produced in an E. coli host.

The invention claimed is:

1. A method for increasing production of heterologous proteins in a bacterial host cell, which comprises co-expressing an effective amount of a polypeptide factor during the expression of said heterologous protein, wherein said polypeptide factor is a metal ion efflux protein derived from a thermophilic eubacterial species which assists in the expression of heterologous proteins.

2. A method according to claim 1, wherein the bacterial host cell is an E. coli host cell.

3. A method according to claim 1 or 2, wherein the thermophilic eubacterial species is Thermus thermophilus.

4. A method according to claim 1 or 2, wherein the polypeptide factor has an amino acid sequence as defined by amino acid position number 1 to amino acid position number 291 of SEQ ID NO: I.

5. A method according to claim 1 or 2, wherein the polypeptide factor has the amino acid sequence of SEQ ID NO: 2.

6. A method according to claim 1 or 2, wherein an isolated DNA sequence encodes for the polypeptide factor.

7. A method according to claim 3, wherein an isolated DNA sequence encodes for the polypeptide factor.

8. A method according to claim 4, wherein an isolated DNA sequence having SEQ ID NO: 3 encodes for the polypeptide factor.

9. A method according to claim 5, wherein an isolated DNA sequence having SEQ ID NO: 4 encodes for the polypeptide factor.

* * * * *

SEQUENCE LISTING

```
<160> NUMBER OF SEQ ID NOS: 9

<210> SEQ ID NO 1
<211> LENGTH: 291
<212> TYPE: PRT
<213> ORGANISM: Thermus thermophilus CzrB

<400> SEQUENCE: 1

Met Ala Glu Gly Ala Ala Arg Leu Ser Leu Val Val Ala Leu Leu Val
1               5                   10                  15

Leu Gly Leu Lys Ala Phe Ala Tyr Leu Leu Thr Gly Ser Val Ala Leu
            20                  25                  30

Leu Ser Asp Ala Leu Glu Ser Leu Val Asn Val Ala Ala Ala Leu Ala
        35                  40                  45

Ala Leu Leu Ala Leu Arg Val Ala Arg Lys Pro Pro Asp Gln Asn His
    50                  55                  60

Pro Phe Gly His Thr Lys Ala Glu Tyr Val Ser Ala Val Leu Glu Gly
65                  70                  75                  80

Val Leu Val Val Leu Ala Ala Leu Trp Ile Ala Arg Glu Ala Leu Pro
                85                  90                  95

Arg Leu Leu His Pro Val Pro Leu Glu Gly Leu Gly Leu Gly Leu Gly
            100                 105                 110

Val Ser Leu Leu Ala Ser Leu Leu Asn Gly Leu Leu Ala Tyr His Leu
        115                 120                 125

Leu Lys Glu Gly Arg Arg His Arg Ser Pro Ala Leu Thr Ala Asp Gly
    130                 135                 140

Tyr His Val Leu Ser Asp Val Leu Thr Ser Leu Gly Val Val Leu Gly
145                 150                 155                 160

Val Gly Leu Ala Gly Leu Thr Gly Leu Trp Val Leu Asp Pro Leu Leu
                165                 170                 175

Ala Leu Ala Val Ala Gly Gln Ile Leu Phe Leu Gly Tyr Arg Ile Val
            180                 185                 190

Arg Glu Ser Val Gly Gly Leu Met Asp Glu Gly Leu Pro Pro Glu Glu
        195                 200                 205

Val Glu Arg Ile Arg Ala Phe Leu Gln Glu Arg Ile Arg Gly Arg Ala
    210                 215                 220

Leu Glu Val His Asp Leu Lys Thr Arg Arg Ala Gly Pro Arg Ser Phe
225                 230                 235                 240

Leu Glu Phe His Leu Val Val Arg Gly Asp Thr Pro Val Glu Glu Ala
                245                 250                 255

His Arg Leu Cys Asp Glu Leu Glu Arg Ala Leu Ala Gln Ala Phe Pro
            260                 265                 270

Gly Leu Gln Ala Thr Ile His Val Glu Pro Glu Gly Glu Arg Lys Arg
        275                 280                 285

Thr Asn Pro
    290

<210> SEQ ID NO 2
<211> LENGTH: 92
<212> TYPE: PRT
```

<213> ORGANISM: Thermus thermophilus CzrB

<400> SEQUENCE: 2

```
Met Asp Glu Gly Leu Pro Pro Glu Val Glu Arg Ile Arg Ala Phe
1               5                   10                  15

Leu Gln Glu Arg Ile Arg Gly Arg Ala Leu Glu Val His Asp Leu Lys
            20                  25                  30

Thr Arg Arg Ala Gly Pro Arg Ser Phe Leu Glu Phe His Leu Val Val
        35                  40                  45

Arg Gly Asp Thr Pro Val Glu Glu Ala His Arg Leu Cys Asp Glu Leu
    50                  55                  60

Glu Arg Ala Leu Ala Gln Ala Phe Pro Gly Leu Gln Ala Thr Ile His
65                  70                  75                  80

Val Glu Pro Glu Gly Glu Arg Lys Arg Thr Asn Pro
                85                  90
```

<210> SEQ ID NO 3
<211> LENGTH: 873
<212> TYPE: DNA
<213> ORGANISM: Thermus thermophilus CzrB

<400> SEQUENCE: 3

| | |
|---|---:|
| atggccgaag gcgccgcccg gttgagcctc gtcgtcgccc tcctcgtctt ggggctcaag | 60 |
| gccttcgcct accttctcac gggctcggtg ccctgctct cggacgccct cgagtccctg | 120 |
| gtgaacgtgg ccgcggccct cgccgccctc ctcgccctcc gggtcgcccg caagccgccg | 180 |
| gaccagaacc accccttcgg ccacaccaag gccgagtacg tttccgccgt cctggaaggg | 240 |
| gtgctggtgg tcttggccgc cctctggatc gccagggagg ccctgccccg cctcctccac | 300 |
| cccgtgcccc tcgagggctt gggcttgggg cttggggtga cctcctcgc ctccctcctc | 360 |
| aacggcctcc tggcctacca cctcctgaag gagggccgcc gccaccgctc ccccgccctc | 420 |
| accgccgacg gtaccacgt cctctccgac gtcctcacct ccttagggggt ggtcctgggc | 480 |
| gtgggcctcg ccgggctcac gggcctttgg gtcttggacc ccctcctcgc cctcgcggtg | 540 |
| gcgggccaga tcctcttcct gggctaccgc atcgtgcggg agtccgtggg agggcttatg | 600 |
| gacgagggcc tccctccgga ggaggtggag cgcatccgcg ccttccttca ggagcgcatc | 660 |
| cggggccggg ccctcgaggt ccacgacctc aagacgcgaa gggccggccc caggagcttc | 720 |
| ctggagttcc acctcgtggt gcgggggac accccgtgg aggaggccca ccgcctctgc | 780 |
| gacgagttgg aaagggccct ggcccaggcc tttccggcc ttcaggccac catccacgtg | 840 |
| gagcccgagg gcgagcggaa gcggacaaac ccc | 873 |

<210> SEQ ID NO 4
<211> LENGTH: 276
<212> TYPE: DNA
<213> ORGANISM: Thermus thermophilus CzrB

<400> SEQUENCE: 4

| | |
|---|---:|
| atggacgagg gcctccctcc ggaggaggtg agcgcatcc gcgccttcct tcaggagcgc | 60 |
| atccgggggcc gggccctcga ggtccacgac ctcaagacgc gaagggccgg ccccaggagc | 120 |
| ttcctggagt tccacctcgt ggtgcggggg gacaccccg tggaggaggc caccgcctc | 180 |
| tgcgacgagt tggaaagggc cctggcccag gcctttccg gccttcaggc caccatccac | 240 |
| gtggagcccg agggcgagcg gaagcggaca aacccc | 276 |

<210> SEQ ID NO 5
<211> LENGTH: 1020
<212> TYPE: DNA
<213> ORGANISM: Thermus thermophilus CzrB

<400> SEQUENCE: 5

```
cctcaagccc aagaaggagg cggtggaaga aggggtctaa atggccgaag gcgccgcccg      60
gttgagcctc gtcgtcgccc tcctcgtctt ggggctcaag gccttcgcct accttctcac     120
gggctcggtg gccctgctct cggacgccct cgagtccctg gtgaacgtgg ccgcggccct     180
cgccgccctc ctcgccctcc gggtcgcccg caagccgccg accagaaacc accccttcgg     240
ccacaccaag gccgagtacg tttccgccgt cctggaaggg gtgctggtgg tcttggccgc     300
cctctggatc gccagggagg ccctgccccg cctcctccac cccgtgcccc tcgagggctt     360
gggcttgggg cttggggtga gcctcctcgc ctccctcctc aacggcctcc tggcctacca     420
cctcctgaag gagggccgcc gccaccgctc cccgccctc accgccgacg ggtaccacgt     480
cctctccgac gtcctcacct ccttaggggt ggtcctgggc gtgggcctcg ccgggctcac     540
gggcctttgg gtcttggacc ccctcctcgc cctcgcggtg gcgggccaga tcctcttcct     600
gggctaccgc atcgtgcggg agtccgtggg agggcttatg gacgagggcc tcctccgga     660
ggaggtggag cgcatccgcg ccttccttca ggagcgcatc cggggccggg ccctcgaggt     720
ccacgacctc aagacgcgaa gggccggccc caggagcttc ctggagttcc acctcgtggt     780
gcggggggac accccgtgg aggagcccca ccgcctctgc gacgagttgg aaagggccct     840
ggcccaggcc tttccggcc ttcaggccac catccacgtg gagcccgagg gcgagcggaa     900
gcggacaaac ccctgacgct cttttcctgc ccggcaaaaa agcgtaaact atgggcaaa     960
ggaggccccc atgcgcagga agcacgactg gctcagggaa acctatagga agagcctgga    1020
```

<210> SEQ ID NO 6
<211> LENGTH: 316
<212> TYPE: PRT
<213> ORGANISM: Ralstonia eutropha CzcD

<400> SEQUENCE: 6

```
Met Gly Ala Gly His Ser His Asp His Pro Gly Gly Asn Glu Arg Ser
1               5                   10                  15

Leu Lys Ile Ala Leu Ala Leu Thr Gly Thr Phe Leu Ile Ala Glu Val
            20                  25                  30

Val Gly Gly Val Met Thr Lys Ser Leu Ala Leu Ile Ser Asp Ala Ala
        35                  40                  45

His Met Leu Thr Asp Thr Val Ala Leu Ala Ile Ala Leu Ala Ala Ile
    50                  55                  60

Ala Ile Ala Lys Arg Pro Ala Asp Lys Lys Arg Thr Phe Gly Tyr Tyr
65                  70                  75                  80

Arg Phe Glu Ile Leu Ala Ala Ala Phe Asn Ala Leu Leu Leu Phe Gly
                85                  90                  95

Val Ala Ile Tyr Ile Leu Tyr Glu Ala Tyr Leu Arg Leu Lys Ser Pro
            100                 105                 110

Pro Gln Ile Glu Ser Thr Gly Met Phe Val Val Ala Val Leu Gly Leu
        115                 120                 125

Ile Ile Asn Leu Ile Ser Met Arg Met Leu Ser Ser Gly Gln Ser Ser
    130                 135                 140

Ser Leu Asn Val Lys Gly Ala Tyr Leu Glu Val Trp Ser Asp Leu Leu
145                 150                 155                 160
```

-continued

```
Gly Ser Val Gly Val Ile Ala Gly Ala Ile Ile Arg Phe Thr Gly
            165                 170                 175

Trp Ala Trp Val Asp Ser Ala Ile Ala Val Leu Ile Gly Leu Trp Val
        180                 185                 190

Leu Pro Arg Thr Trp Ile Leu Leu Lys Ser Ser Leu Asn Val Leu Leu
        195                 200                 205

Glu Gly Val Pro Asp Val Asp Leu Ala Glu Val Glu Lys Gln Ile
210                 215                 220

Leu Ala Thr Pro Gly Val Lys Ser Phe His Asp Leu His Ile Trp Ala
225                 230                 235                 240

Leu Thr Ser Gly Lys Ala Ser Leu Thr Val His Val Val Asn Asp Thr
            245                 250                 255

Ala Val Asn Pro Glu Met Glu Val Leu Pro Glu Leu Lys Gln Met Leu
            260                 265                 270

Ala Asp Lys Phe Asp Ile Thr His Val Thr Ile Gln Phe Glu Leu Ala
        275                 280                 285

Pro Cys Glu Gln Ala Asp Ala Ala Gln His Phe Asn Ala Ser Pro Ala
        290                 295                 300

Leu Val Gly Ser Lys Ser Leu Ala Ala Gly Gly Asn
305                 310                 315

<210> SEQ ID NO 7
<211> LENGTH: 325
<212> TYPE: PRT
<213> ORGANISM: Staphylococcus aureus CzrB

<400> SEQUENCE: 7

Met Ser His Ser His His Asp His Met His Ser His Val Thr Thr
1               5                   10                  15

Asp Asn Lys Lys Val Leu Phe Ile Ser Phe Leu Ile Ile Gly Leu Tyr
                20                  25                  30

Met Phe Ile Glu Ile Ile Gly Gly Leu Leu Ala Asn Ser Leu Ala Leu
            35                  40                  45

Leu Ser Asp Gly Ile His Met Phe Ser Asp Thr Phe Ser Leu Gly Val
50                  55                  60

Ala Leu Val Ala Phe Ile Tyr Ala Glu Lys Asn Ala Thr Thr Thr Lys
65                  70                  75                  80

Thr Phe Gly Tyr Lys Arg Phe Glu Val Leu Ala Ala Leu Phe Asn Gly
                85                  90                  95

Val Thr Leu Phe Val Ile Ser Ile Leu Ile Val Phe Glu Ala Ile Lys
            100                 105                 110

Arg Phe Phe Val Pro Ser Glu Val Gln Ser Lys Glu Met Leu Ile Ile
        115                 120                 125

Ser Ile Ile Gly Leu Ile Val Asn Ile Val Val Ala Phe Phe Met Phe
130                 135                 140

Lys Gly Gly Asp Thr Ser His Asn Leu Asn Met Arg Gly Ala Phe Leu
145                 150                 155                 160

His Val Ile Gly Asp Leu Leu Gly Ser Val Gly Ala Ile Thr Ala Ala
            165                 170                 175

Ile Leu Ile Trp Ala Phe Gly Trp Thr Ile Ala Asp Pro Ile Ala Ser
        180                 185                 190

Ile Leu Val Ser Val Ile Ile Leu Lys Ser Ala Trp Gly Ile Thr Lys
            195                 200                 205

Ser Ser Ile Asn Ile Leu Met Glu Gly Thr Pro Ser Asp Val Asp Ile
        210                 215                 220
```

```
Asp Glu Val Ile Thr Thr Ile Lys Lys Asp Ser Arg Ile Gln Ser Val
225                 230                 235                 240

His Asp Cys His Val Trp Thr Ile Ser Asn Asp Met Asn Ala Leu Ser
            245                 250                 255

Cys His Val Val Val Asp His Thr Leu Thr Met Lys Glu Cys Glu Leu
            260                 265                 270

Leu Leu Glu Asn Ile Glu His Asp Leu Leu His Leu Asn Ile His His
            275                 280                 285

Met Thr Ile Gln Leu Glu Thr Pro Asn His Lys His Asp Glu Ser Ile
290                 295                 300

Ile Cys Ser Gly Thr His Ser His Ser His Asn His His Ala His His
305                 310                 315                 320

His Ala His Val His
            325

<210> SEQ ID NO 8
<211> LENGTH: 507
<212> TYPE: PRT
<213> ORGANISM: Rattus norvegicus Znt1

<400> SEQUENCE: 8

Met Gly Cys Trp Gly Arg Asn Arg Gly Arg Leu Leu Cys Met Leu Leu
1               5                   10                  15

Leu Thr Phe Met Phe Met Val Leu Glu Val Val Val Ser Arg Val Thr
                20                  25                  30

Ala Ser Leu Ala Met Leu Ser Asp Ser Phe His Met Leu Ser Asp Val
            35                  40                  45

Leu Ala Leu Val Val Ala Leu Val Ala Glu Arg Phe Ala Arg Arg Thr
        50                  55                  60

His Ala Thr Gln Lys Asn Thr Phe Gly Trp Ile Arg Ala Glu Val Met
65                  70                  75                  80

Gly Ala Leu Val Asn Ala Ile Phe Leu Thr Gly Leu Cys Phe Ala Ile
                85                  90                  95

Leu Leu Glu Ala Val Glu Arg Phe Ile Glu Pro His Glu Met Gln Gln
            100                 105                 110

Pro Leu Val Val Leu Ser Val Gly Val Ala Gly Leu Leu Val Asn Val
        115                 120                 125

Leu Gly Leu Cys Leu Phe His His His Ser Gly Glu Gly Gln Gly Ala
130                 135                 140

Gly His Gly His Ser His Gly His Gly His His Leu Ala Lys Gly
145                 150                 155                 160

Ala Arg Lys Ala Gly Arg Ala Gly Gly Glu Ala Gly Ala Pro Pro Gly
            165                 170                 175

Arg Ala Pro Asp Gln Glu Pro Asp Gln Glu Thr Asn Thr Leu Val
        180                 185                 190

Ala Asn Thr Ser Asn Ser Asn Gly Leu Lys Ala Asp Gln Ala Glu Pro
            195                 200                 205

Glu Lys Leu Arg Ser Asp Asp Pro Val Asp Val Gln Val Asn Gly Asn
        210                 215                 220

Leu Ile Gln Glu Ser Asp Ser Leu Glu Ser Glu Asp Asn Arg Ala Gly
225                 230                 235                 240

Gln Leu Asn Met Arg Gly Val Phe Leu His Val Leu Gly Asp Ala Leu
            245                 250                 255
```

```
Gly Ser Val Ile Val Val Asn Ala Leu Val Phe Tyr Phe Ser Trp
            260                 265                 270
Lys Gly Cys Thr Glu Asp Asp Phe Cys Val Asn Pro Cys Phe Pro Asp
        275                 280                 285
Pro Cys Lys Ser Ser Val Glu Leu Met Asn Ser Thr Gln Ala Pro Met
290                 295                 300
His Glu Ala Gly Pro Cys Trp Val Leu Tyr Leu Asp Pro Thr Leu Cys
305                 310                 315                 320
Ile Ile Met Val Cys Ile Leu Leu Tyr Thr Thr Tyr Pro Leu Leu Lys
                325                 330                 335
Glu Ser Ala Leu Ile Leu Leu Gln Thr Val Pro Lys Gln Ile Asp Ile
            340                 345                 350
Lys His Leu Val Lys Glu Leu Arg Asp Val Glu Gly Val Glu Glu Val
        355                 360                 365
His Glu Leu His Val Trp Gln Leu Ala Gly Ser Arg Ile Ile Ala Thr
370                 375                 380
Ala His Ile Lys Cys Glu Asp Pro Ala Ser Tyr Met Gln Val Ala Lys
385                 390                 395                 400
Thr Ile Lys Asp Val Phe His Asn His Gly Ile His Ala Thr Thr Ile
                405                 410                 415
Gln Pro Glu Phe Ala Ser Val Gly Ser Lys Ser Ser Val Pro Cys
            420                 425                 430
Glu Leu Ala Cys Arg Thr Gln Cys Ala Leu Lys Gln Cys Cys Gly Thr
        435                 440                 445
Arg Pro Gln Val His Ser Gly Lys Glu Ala Glu Lys Ala Pro Thr Val
    450                 455                 460
Ser Ile Ser Cys Leu Glu Leu Ser Glu Asn Leu Glu Lys Lys Pro Arg
465                 470                 475                 480
Arg Thr Lys Ala Glu Gly Ser Val Pro Ala Val Val Ile Glu Ile Lys
                485                 490                 495
Asn Val Pro Asn Lys Gln Pro Glu Ser Ser Leu
            500                 505

<210> SEQ ID NO 9
<211> LENGTH: 442
<212> TYPE: PRT
<213> ORGANISM: Saccharomyces cerevisiae Zrc1

<400> SEQUENCE: 9

Met Ile Thr Gly Lys Glu Leu Arg Ile Ile Ser Leu Leu Thr Leu Asp
1               5                   10                  15
Thr Val Phe Phe Leu Leu Glu Ile Thr Ile Gly Tyr Met Ser His Ser
            20                  25                  30
Leu Ala Leu Ile Ala Asp Ser Phe His Met Leu Asn Asp Ile Ile Ser
        35                  40                  45
Leu Leu Val Ala Leu Trp Ala Val Asp Val Ala Lys Asn Arg Gly Pro
    50                  55                  60
Asp Ala Lys Tyr Thr Tyr Gly Trp Lys Arg Ala Glu Ile Leu Gly Ala
65                  70                  75                  80
Leu Ile Asn Ala Val Phe Leu Ile Ala Leu Cys Phe Ser Ile Met Ile
                85                  90                  95
Glu Ala Leu Gln Arg Leu Ile Glu Pro Gln Glu Ile Gln Asn Pro Arg
            100                 105                 110
Leu Val Leu Tyr Val Gly Val Ala Gly Leu Ile Ser Asn Val Val Gly
        115                 120                 125
```

-continued

```
Leu Phe Leu Phe His Asp His Gly Ser Asp Ser Leu His Ser His Ser
        130                 135                 140

His Gly Ser Val Glu Ser Gly Asn Asn Asp Leu Asp Ile Glu Ser Asn
145                     150                 155                 160

Ala Thr His Ser His Ser His Ala Ser Leu Pro Asn Asp Asn Leu Ala
                165                 170                 175

Ile Asp Glu Asp Ala Ile Ser Ser Pro Gly Pro Ser Gly Gln Ile Gly
            180                 185                 190

Glu Val Leu Pro Gln Ser Val Val Asn Arg Leu Ser Asn Glu Ser Gln
                195                 200                 205

Pro Leu Leu Asn His Asp Asp His Asp His Ser His Glu Ser Lys Lys
        210                 215                 220

Pro Gly His Arg Ser Leu Asn Met His Gly Val Phe Leu His Val Leu
225                 230                 235                 240

Gly Asp Ala Leu Gly Asn Ile Gly Val Ile Ala Ala Ala Leu Phe Ile
                245                 250                 255

Trp Lys Thr Glu Tyr Ser Trp Arg Tyr Tyr Ser Asp Pro Ile Val Ser
                260                 265                 270

Leu Ile Ile Thr Ile Ile Ile Phe Ser Ser Ala Leu Pro Leu Ser Arg
                275                 280                 285

Arg Ala Ser Arg Ile Leu Leu Gln Ala Thr Pro Ser Thr Ile Ser Ala
        290                 295                 300

Asp Gln Ile Gln Arg Glu Ile Leu Ala Val Pro Gly Val Ile Ala Val
305                 310                 315                 320

His Asp Phe His Val Trp Asn Leu Thr Glu Ser Ile Tyr Ile Ala Ser
                325                 330                 335

Ile His Val Gln Ile Asp Cys Ala Pro Asp Lys Phe Met Ser Ser Ala
        340                 345                 350

Lys Leu Ile Arg Lys Ile Phe His Gln His Gly Ile His Ser Ala Thr
        355                 360                 365

Val Gln Pro Glu Phe Val Ser Gly Asp Val Asn Glu Asp Ile Arg Arg
        370                 375                 380

Arg Phe Ser Ile Ile Ala Gly Gly Ser Pro Ser Ser Ser Gln Glu Ala
385                 390                 395                 400

Phe Asp Ser His Gly Asn Thr Glu His Gly Arg Lys Lys Arg Ser Pro
                405                 410                 415

Thr Ala Tyr Gly Ala Thr Thr Ala Ser Ser Asn Cys Ile Val Asp Asp
                420                 425                 430

Ala Val Asn Cys Asn Thr Ser Asn Cys Leu
                435                 440
```